United States Patent [19]
Takase

[11] Patent Number: 5,221,036
[45] Date of Patent: Jun. 22, 1993

[54] SURGICAL STAPLER

[76] Inventor: Haruo Takase, 20-16, Shimoochiai 3-chome, Shinjuku-ku, Tokyo, Japan

[21] Appl. No.: 898,400

[22] Filed: Jun. 11, 1992

Related U.S. Application Data

[63] Continuation of Ser. No. 713,284, Jun. 11, 1991, abandoned.

[51] Int. Cl.$^5$ .............................. A61B 17/072
[52] U.S. Cl. ........................ 227/19; 227/176; 227/178; 227/113
[58] Field of Search ................. 227/19, 175, 176, 177, 227/178, 179, 181, 113

[56] References Cited

U.S. PATENT DOCUMENTS

| | | |
|---|---|---|
| 2,219,739 | 10/1940 | Duncan .............................. 227/113 |
| 3,079,608 | 3/1963 | Babkin .............................. 227/19 |
| 3,315,863 | 4/1967 | O'Dea .............................. 227/19 |
| 4,111,206 | 9/1978 | Vishnevsky et al. ............ 227/176 |
| 4,305,539 | 12/1981 | Korolkov et al. ................. 227/19 |
| 4,633,874 | 1/1987 | Chow et al. ..................... 227/176 |
| 4,776,506 | 10/1988 | Green ............................. 227/19 |

FOREIGN PATENT DOCUMENTS

| | | |
|---|---|---|
| 63-270040 | 11/1988 | Japan . |
| 1-62810 | 4/1989 | Japan . |
| 8300614 | 8/1981 | PCT Int'l Appl. ................ 227/178 |

*Primary Examiner*—Frank T. Yost
*Assistant Examiner*—Allan M. Schrock
*Attorney, Agent, or Firm*—Wenderoth, Lind & Ponack

[57] ABSTRACT

A surgical suturing stapler uses a staple cartridge for containing substantially U-shaped staples, which cartridge can be detachably fitted into a cartridge holder placed between two jaws. The staples can be easily loaded into the staple cartridge by detaching the cartridge from the stapler. When closing the jaws between which the stapler cartridge is placed, the staples in the cartridge are discharged and inserted into bodily tissues or the like to be sutured. By using the staple cartridge magnetized, the staples of metallic material are magnetically retained within the staple cartridge.

9 Claims, 6 Drawing Sheets

SURGICAL STAPLER

This application is a Rule 1.62 continuation of now abandoned application, Ser. No. 07/713,284, filed Jun. 11, 1991.

BACKGROUND OF THE INVENTION

1. Field of the Invention

This invention relates to a surgical stapler for suturing tissues in a surgical operation with square U-shaped staples, and more particularly to a surgical suturing stapler capable of being readily loaded with staples by use of a detachable staple cartridge.

2. Description of the Prior Art

The inventor of this invention has formerly proposed surgical suturing staplers for inserting square U-shaped staples into a bodily part to stitch a wound or the like and arrest hemorrhage. (Japanese Patent Public Discl. No. SHO 63(1988)-270040(A) and Japanese U.M. Pub. Discl. No. HEI 1(1990)-62810(A))

Figures 1, 2, 3:
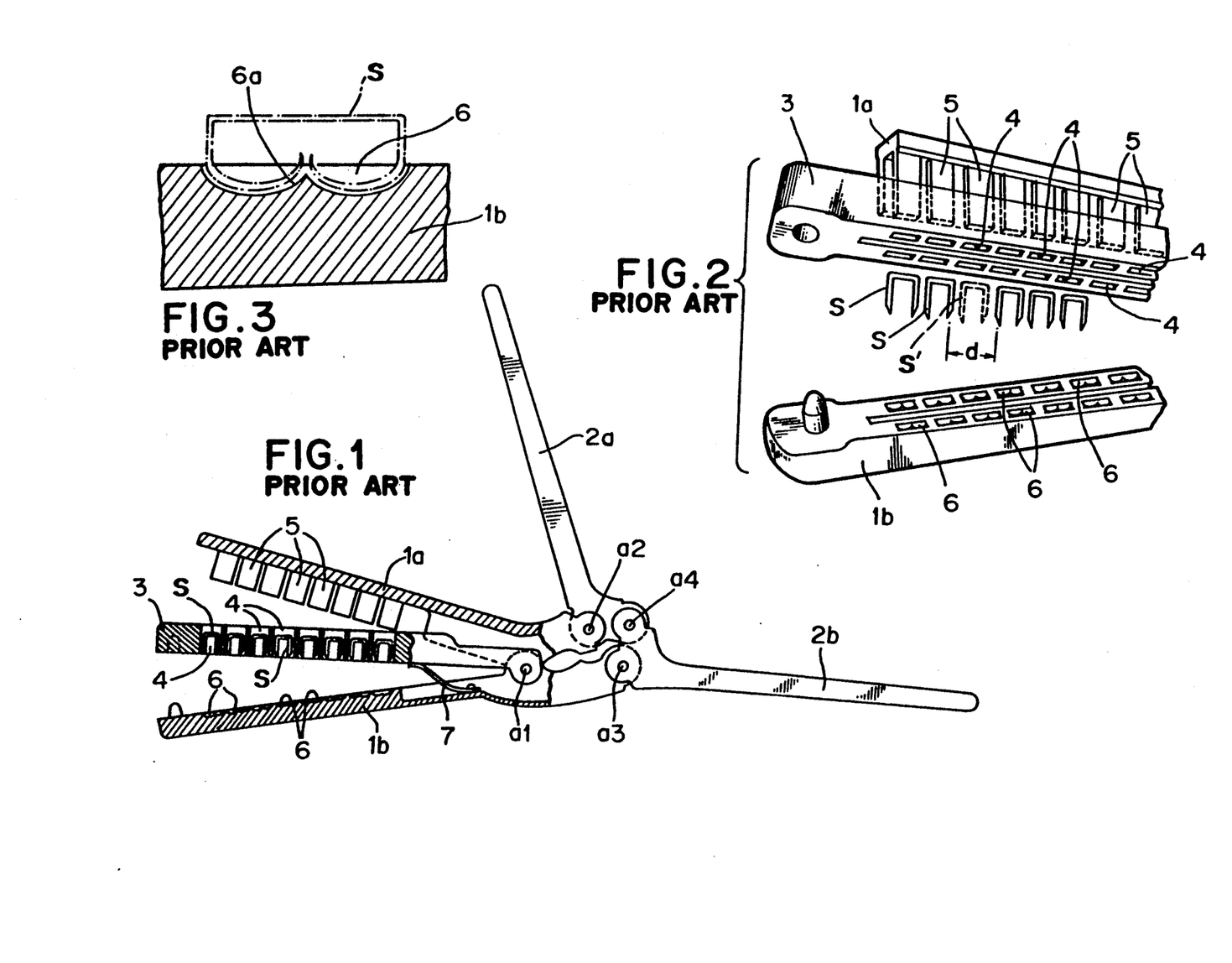
FIG. 1 is a side view, partly in section, of a prior art surgical stapler.
FIG. 2 is a partially enlarged perspective view of FIG. 1.
FIG. 3 is an enlarged vertical section of an anvil groove in the stapler of FIG. 1.

The prior art surgical staplers including the staplers proposed by the inventor as noted above can discharge a number of U-shaped staples in one lot into a bodily part as illustrated in FIGS. 1 and 2. The stapler of this type comprises a pair of jaws $1a$, $1b$ pivotally supported by an axial pin $a1$, a pair of handles $2a$, $2b$ having tip portions rotatably connected to the jaws $1a$, $1b$ through axial pins $a2$, $a3$ and pivotally supported by an axial pin $a4$, and a staple magazine 3. As shown in FIG. 2, two parallel rows of staple chambers 4 in which the staples (S) are loaded are formed in the staple magazine 3.

The upper jaw $1a$ has extruding pieces 5 to be plunged into the staple chambers 4 in the staple magazine 3 to push the staples (S) out of the staple chambers 4 toward the lower jaw $1b$. The lower jaw $1b$ is provided in its upper surface with anvil grooves 6 opposite to the staple chambers 4 in the staple magazine so as to bend inwardly the legs of each staple (S) being thrust thereinto.

A bodily part such as the edges of a wound in a surgical operation can be sutured with the staples (S) merely by gripping the handles $2a$, $2b$ while putting the bodily part between the upper and lower jaws $1a$ and $1b$. By gripping the handles $2a$, $2b$, the upper and lower jaws $1a$, $1b$ are rotated around the axial pin $a1$ and closed to force the staples out of the staple chambers 4. The staples thus forced out are pressed against the lower jaw $1b$ to cause the legs of the staples to be thrust into the anvil grooves 6 and bent inwardly. Thus, the tissues are kept in a state pressed with the staples so as to arrest hemorrhage.

The surgical stapler noted above provides advantageous suturing of the tissues of a living body, as even a large incision part can be easily stitched with a number of staples in one operation. This stapler has been found a big help in a surgical operation requiring prompt treatment, but is disadvantageous in that the work of being loaded with the staples (S) turns out to be a very troublesome chore in a surgical operation. That is, the staples (S) must be inserted one by one into the staple chambers 4 formed in the staple magazine 3 by hand while the upper and lower jaws $1a$, $1b$ are opened as wide as possible. This work requires much time and labor and proves to be troublesome, so that it is substantially impossible to load the staple magazine with the staples during an operation.

Furthermore, the conventional surgical stapler entails problems such as difficulty in visually discerning whether the staples are infallibly placed in all the staple chambers 4 of the staple magazine. There is a possibility that a staple may fall out of the staple chamber in the magazine accidentally, suffering a disadvantage that a wound or other possible tissues would be incompletely sutured due to the falling out of the staple. For instance, when the staple (S') as shown in FIG. 2 fails to be charged in or falls out of the staple chamber, the part (d) indicated in the drawing cannot provide the effects of suturing tissues and arresting hemorrhage.

In the surgical stapler of this type, the staple is retained inside the staple chamber 4 by frictional force produced by the inner surrounding surface of the staple chamber. However, the friction force by which the staple is retained would gradually decrease during the course of prolonged service, and therefore, the staple retained would easily fall out of the staple chamber with slight shock or other possible external force.

The anvil groove 6 formed in the lower jaw $1b$ of the conventional surgical stapler has a bottom surface $6a$ shaped in a substantial $\omega$ as shown in FIG. 3. The staple being thrust into the anvil groove is bent inwardly along the bottom surface $6a$ of the anvil groove 6 with the pointed ends of the legs being curved upwardly, as indicated by imaginary lines in the drawing. Namely, the staple is bent in a general B-shape. Therefore, the grasping force at the central portion of the bent staple becomes weaker, so that the effect of arresting hemorrhage at that portion would be reduced. Thus, the conventional stapler entails disadvantages in that the staples cannot be readily loaded nor reliably retained within the staple chambers in the staple magazine, and the legs of the staples cannot be bent suitably, thereby suturing tissues incompletely.

SUMMARY OF THE INVENTION

In view of the drawbacks of the conventional surgical stapler as mentioned above, it is an object of the present invention is to provide a surgical suturing stapler capable of being readily and promptly loaded with staples even in the middle of a surgical operation and securely retaining the staples.

Another object of the present invention is to provide a surgical stapler having a staple cartridge capable of reliably retaining staples therein and visually discerning the retained staples so as to suture tissues infallibly.

A further object of the present invention is to provide a surgical stapler capable of suitably bending the legs of the staples inserted into tissues to bring about an effect of steadily arresting hemorrhage.

To accomplish the objects mentioned above, the surgical stapler according to the present invention comprises a first jaw having stapler extruding pieces, a second jaw having anvil grooves, a cartridge holding member placed between the first and second jaws for retaining a staple cartridge to be loaded with staples, which staple cartridge has staple chambers for containing the staples therein.

Upon permitting the staple cartridge to be loaded with the staples and fitted into the cartridge holding member, the staples are discharged out of the cartridge by the stapler extruding pieces which are thrust into the staple chambers in the staple cartridge when the first and second jaws are closed. The legs of the staples thus discharged pierce through tissues or the like interposed between the staple cartridge and the second jaw and are forced into the anvil grooves to thereby be bent inwardly.

Since the staple cartridge is detachably fitted into the cartridge holding member, the staples can easily be inserted in the staple cartridge and visually discerned.

By using a magnetic staple cartridge which is magnetized, the staples loaded into the staple cartridge are magnetically retained to be prevented from falling out of the staple cartridge accidentally.

BRIEF DESCRIPTION OF THE DRAWINGS

Other objects and features of the present invention will now be explained in detail with reference to the accompanying drawings, wherein.

DESCRIPTION OF THE PREFERRED EMBODIMENTS

Figure 4:
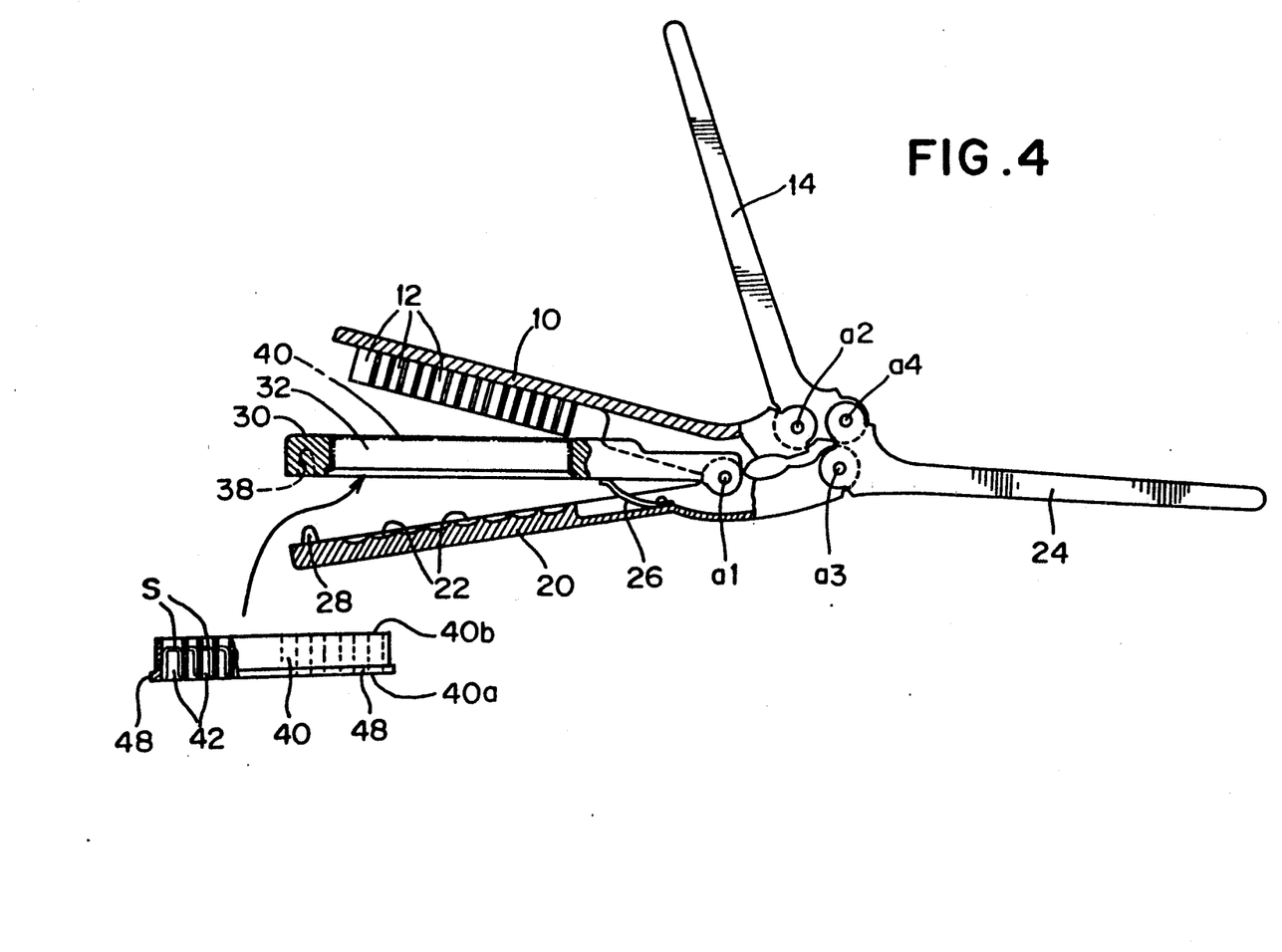
FIG. 4 is a partly sectional side view showing one embodiment of a surgical stapler according to the present invention.

One embodiment of the surgical suturing stapler with a detachable staple cartridge according to this invention will be described below with reference to FIGS. 4 and 5.

The surgical stapler comprises a first jaw 10 provided on one surface 10a thereof with a plurality of staple extruding pieces 12; a second jaw 20 having a plurality of anvil grooves 22 formed in a surface 20a opposite to the surface on which the staple extruding pieces 12 are planted on the first jaw 10; a cartridge holding member 30 having a cartridge hole 32, which is placed between the first and second jaws 10 and 20; and a staple cartridge 40 having a plurality of staple chambers 42 for containing staples (S), which is detachably fitted into the cartridge hole 32 of the cartridge holding member 30.

The first and second jaws 10, 20 and cartridge holding member 30 are pivoted around an axial pin a1. The first jaw 10 is pivotally connected to a handle 14 through an axial pin a2, and the second jaw 20 is pivotally connected to a handle 24 through an axial pin a3. The handles 14, 24 are pivoted around an axial pin a4. Thus, the parts linking the pins a1-a4 constitute a lever structure shaped in a general pantograph, so that the first and second jaws 10, 20 can be forcibly closed by grasping the handles 14, 24. Though the jaws 10, 20 are respectively separated from the corresponding handles 14, 24 in this embodiment, the jaw 10 may however be integrally connected to the handle 14, and the jaw 20 may be integrally connected to the handle 24. In this structure, the aforenoted axial pins a2-a4 can be omitted.

The staple cartridge 40 which is fitted into the cartridge hole 32 in the cartridge holding member 30 is generally held by frictional force brought about by the inner surrounding surface of the cartridge hole 32. However, in order to more steadily hold the cartridge within the cartridge hole 32, a spring or other possible means for positively securing the cartridge 40 within the cartridge hole 32 may be assembled inside the cartridge holding member 30.

The cartridge holding member 30 is urged toward the first jaw 10 by a spring 26 having one end fixed on the second jaw 20 so that the space between the second jaw 20 and the cartridge holding member 30 can be made wide to facilitate an object, such as, bodily tissue to be sutured, being put there.

The staple chamber 42 in the staple cartridge 40 is substantially equal in plain geometric shape to the staple (S) so as to securely retain the staple within the staple chamber 42. The height of the staple chamber 42 is somewhat larger than that of the staple and nearly equal to that of the staple cartridge 40.

Figure 5:
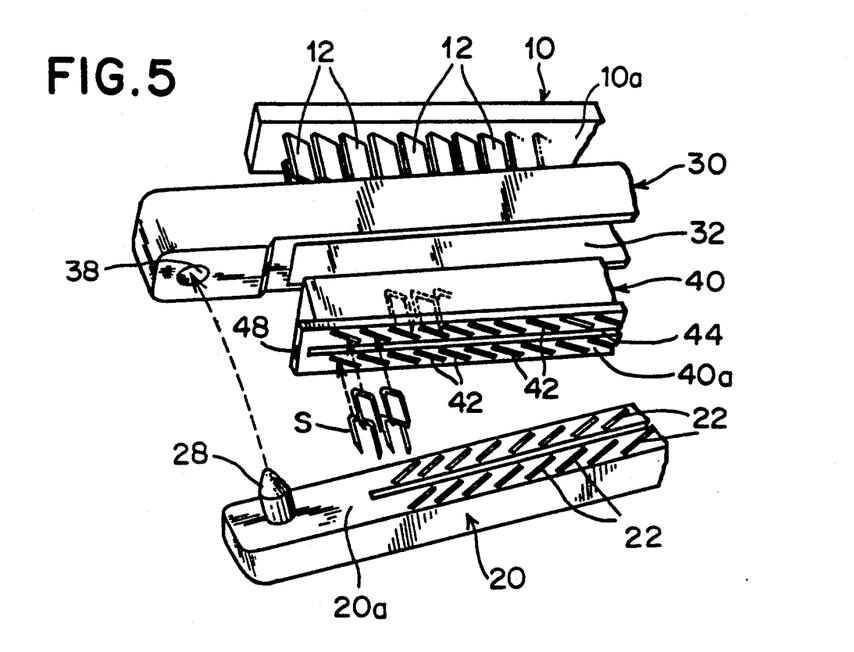
FIG. 5 is a partially enlarged perspective view of the stapler of FIG. 4.

The staple chambers 42 are arranged aslant in plane relative to the lengthwise direction of the cartridge holding member as illustrated in FIG. 5, and may preferably be brought closer to the adjacent ones in order to diminish the pitch at which the staples are inserted through the object to be sutured. By forming the staple chambers as close as possible, the object such as bodily surfaces can be sufficiently sutured if one of the staples loaded into the staple cartridge 40 falls off accidentally.

In this embodiment, two rows of the staple chambers 42 arranged aslant as noted above are formed across a ditch 44 for disjoining the rows of staple chambers 42.

Reference numeral 28 denotes a positioning projection formed on the leading portion of the second jaw 20. When the jaws 10, 20 are closed, the projection 28 is fitted into a hole 38 bored in the lower surface of the leading portion of the cartridge holding member 30, so that the position of the cartridge holding member 30 relative to the second jaw 20 can be decided with accuracy.

Figures 6, 7:
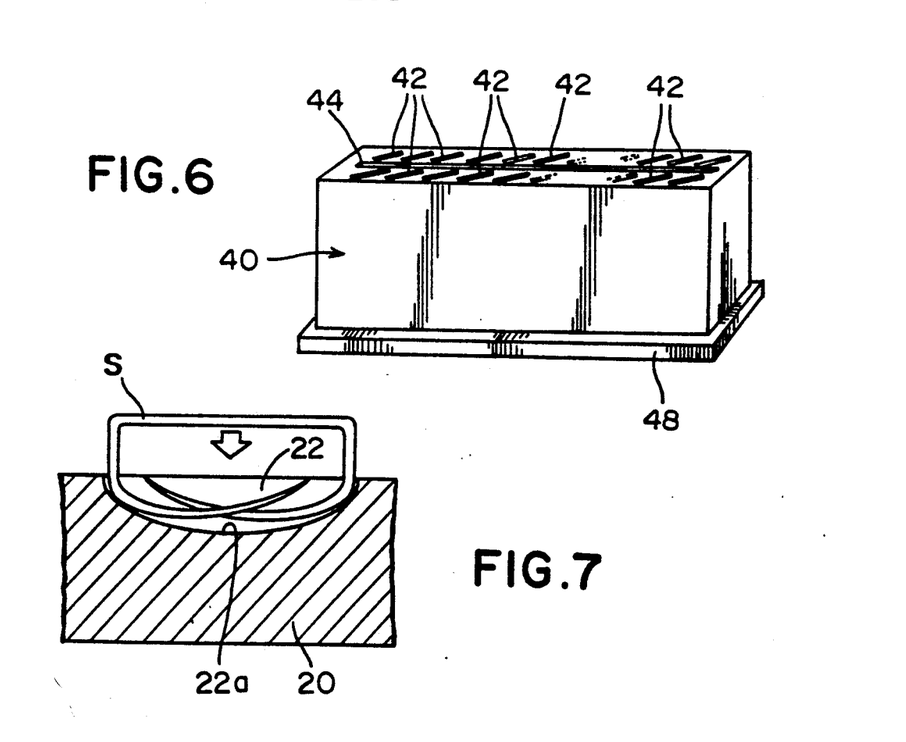
FIG. 6 is a perspective view of a staple cartridge used in the stapler shown in FIG. 4.
FIG. 7 is a sectional view of an anvil groove in another embodiment of this invention.

As shown in FIG. 6, the staple cartridge 40 has a flange 48 which is received by a step portion formed in the lower surface 30a of the cartridge holding member 30. Due to the flange 48, the cartridge 40 is prevented from passing through the cartridge hole 32 in the cartridge holding member 30. The lower surface 40a of the staple cartridge 40 comes into parallel contact with the upper surface 20a of the second jaw 20 when the first and second jaws 10 and 20 are closed around the axial pin a1.

The anvil grooves 22 are formed in positions which face the staple chambers 42 in the cartridge 40 fitted into the cartridge hole 32 of the cartridge holding member 30 when bringing a lower surface 40a of the cartridge 40 in face to face contact with the upper surface 20a of the second jaw 20. The bottom surface 22a of the anvil groove 22 formed in the second jaw 20 assumes an arc shape as shown FIG. 7. As can be seen from FIG. 7, arc-shaped bottom surface 22a has a length substantially equal to the height of the leg portion of a staple 27.

Figure 8A:
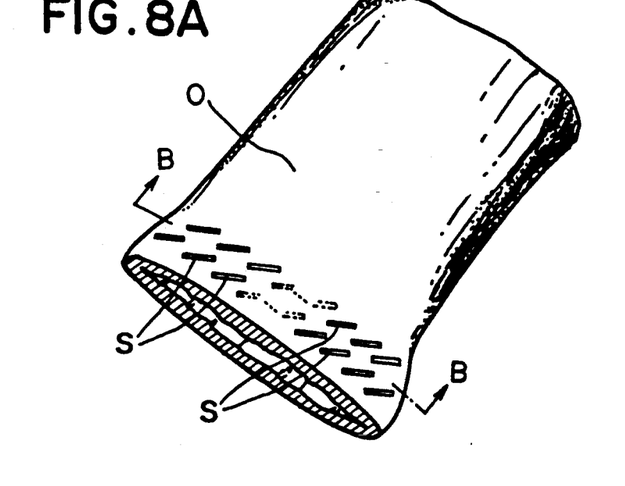
FIGS. 8A and 8B are a perspective view and a sectional view taken along B—B in FIG. 8A, respectively showing the state in which bodily tissue is sutured with the staples according to this invention.
Figure 8B:
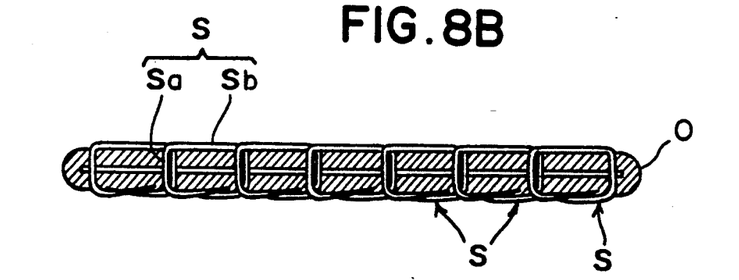

When the jaws 10, 20 are closed, the staple extruding pieces 12 on the first jaw 10 are plunged into the staple chambers 42 of the cartridge 40 fitted into the cartridge hole 32 of the cartridge holding member 30, consequently discharging the staples (S) out of the staple chambers 42 toward the second jaw 20. The staples thus discharged are thrust into the anvil grooves 22 of the second jaw 20 to cause the leg portions of the staples to be bent inwardly along the bottom surfaces of the anvil grooves 22 as shown in FIG. 7. If there is an object such as bodily tissues between the cartridge holding member 30 and the second jaw 20 when discharging the staples, the object (O) is sutured with staples as shown in FIG. 8A. The leg portions (Sa) of the staple (S) piercing the object (O) are inwardly bent and become substantially in parallel with the plane portion (Sb) of the staple as shown in FIG. 8B, so as to press the object uniformly over the entire area with the leg portions (Sa). Thus, the bodily tissue is sutured with uniform press force, to insure complete arrest of hemorrhage.

Figure 9:
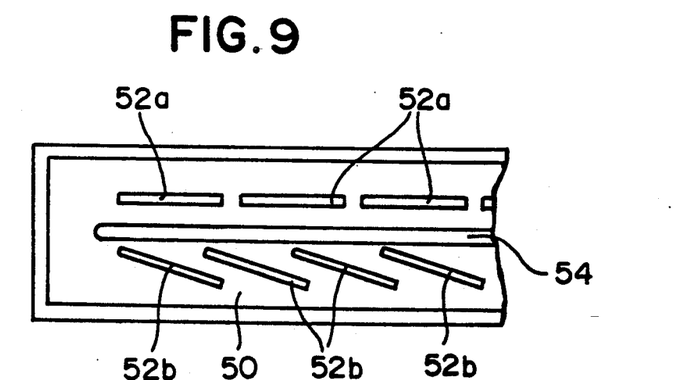
FIG. 9 is a partly plan view of the staple cartridge in still another embodiment of this invention.

Though two rows of staple chambers 42 arranged aslant are formed in the staple cartridge 40 in the foregoing embodiment, this structure should not be understood as limitative. For example, as shown in FIG. 9, the staple cartridge 50 may be provided across a disjoining ditch 54 with one row of staple chambers 52a arranged in a straight line and another row of staple chambers 52b arranged aslant. Since the tissue on the side sutured by the staples discharged from the staple chambers 52a becomes useless after the operation, the staple chambers 52a may be arranged straight.

Figures 10, 11, 12:
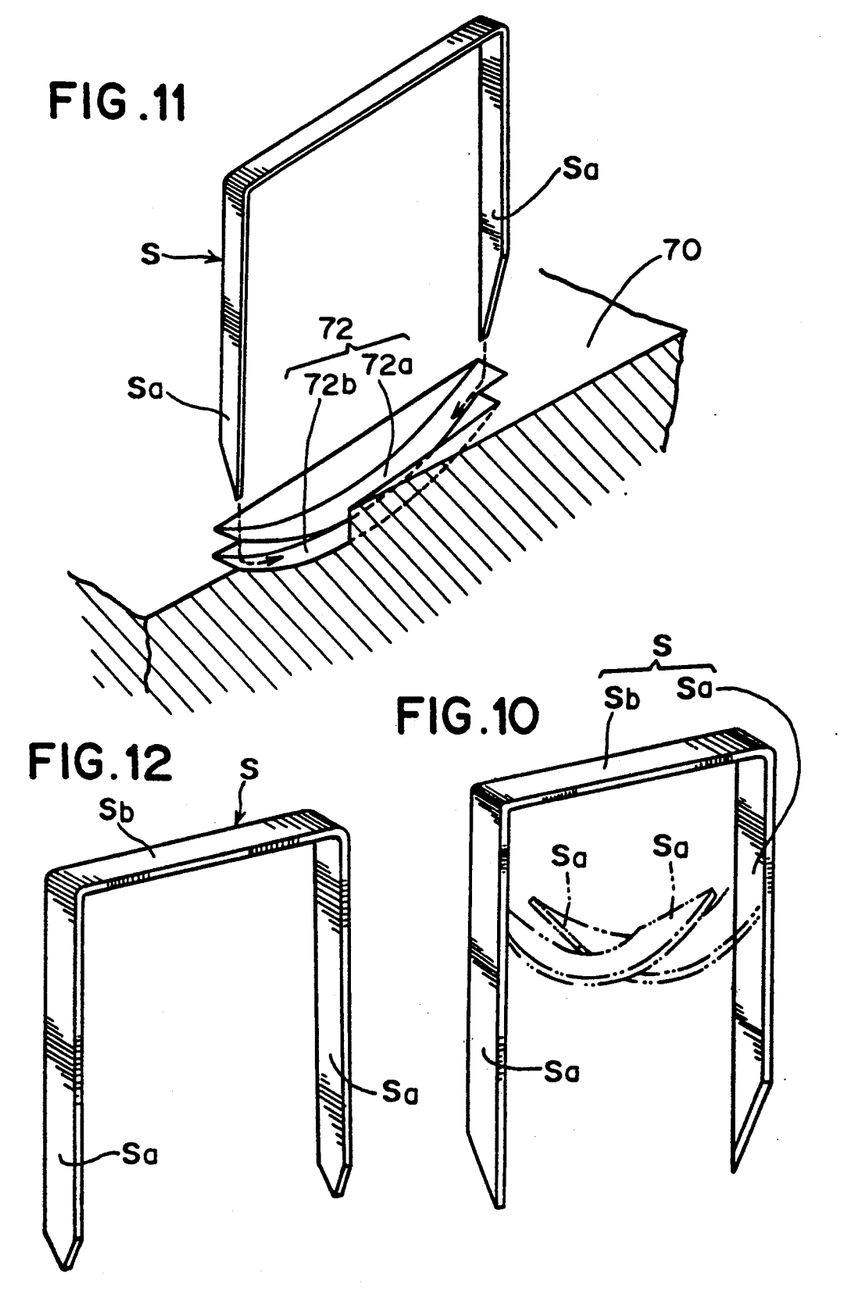
FIG. 10 is a perspective view of a staple according to this invention.
FIG. 11 is a partially cutaway, enlarged perspective view of an anvil groove in yet another embodiment of this invention.
FIG. 12 is a perspective view showing a staple in a further embodiment of this invention.

The leg portions (Sa) of the staple (S) each has a sharply pointed end as shown in FIG. 10. The leg portions must be designed so as not to interfere with each other when being bent within the anvil groove 22 in the second jaw 20. To attain this purpose, there may be adopted a structure as shown in FIG. 11. That is, an anvil groove 72 in a second jaw 70 is constituted by two adjoining guide grooves 72a and 72b which are staggered from each other, so that one of the legs (Sa) is guided by the guide groove 72a, and the other leg is guided by the guide groove 72b when being thrust into the anvil grooves 22. With this anvil groove, the legs of the staple are suitably bent along the respective guide grooves without colliding with each other, as indicated by the imaginary line in FIG. 10.

To prevent the legs of the staple from colliding with each other when being thrust into the anvil groove formed in the second jaw, the legs of the staple may be sharpened in a wedge shape as shown in FIG. 12. This staple with sharply pointed ends also facilitates insertion into the objects, such as bodily tissues, to be sutured. Furthermore, it is required to make the legs (Sa) of the staple sufficiently longer than the plane portion (Sb), so that the object such as tissues can be stably and reliably sutured.

Figure 13:
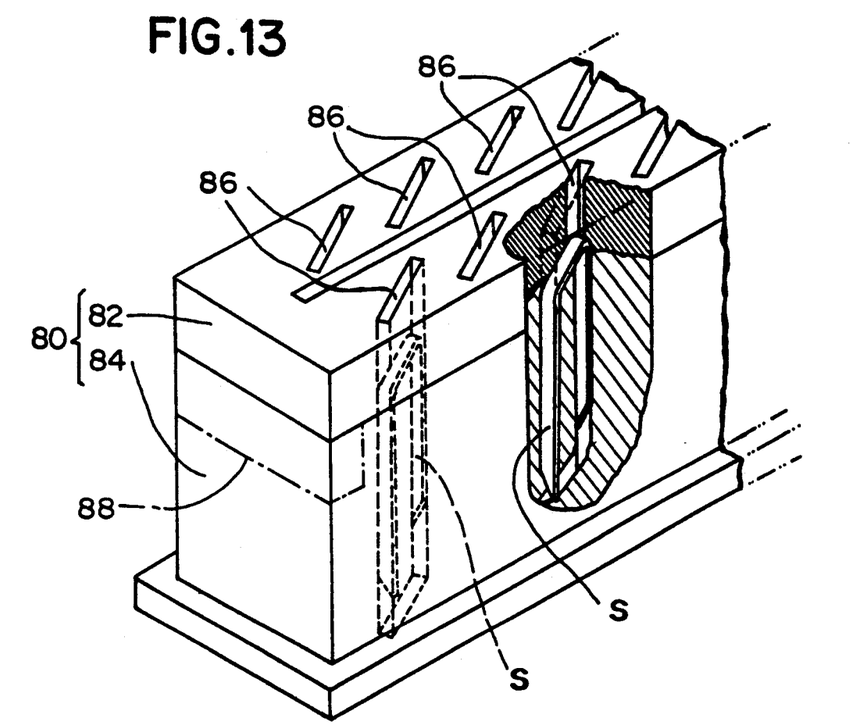
FIG. 13 is a partially cutaway, enlarged perspective view of a staple cartridge in a still further embodiment of this invention.

Next, a structure capable of steadily holding the staples in the staple magazine will be described with reference to FIG. 13.

A staple cartridge 80 in this embodiment comprises a magnet member 82 and a cartridge body 84 of non-magnetic material. There are formed staple chambers 86 through the united magnet member 82 and cartridge body 84. The staples (S) which are generally made of metal and inserted into the staple chambers 86 are steadily held within the staple chambers 86 by magnetic attracting force produced by the magnet member 82. Thus, the staples magnetically held within the cartridge can no longer fall out of the staple chambers accidentally.

Though the staple cartridge 80 has the magnet member 82 as noted above in the illustrated embodiment, the entire staple cartridge as shown in FIG. 6 may of course be made of magnetic material and magnetized.

Figures 14, 15:
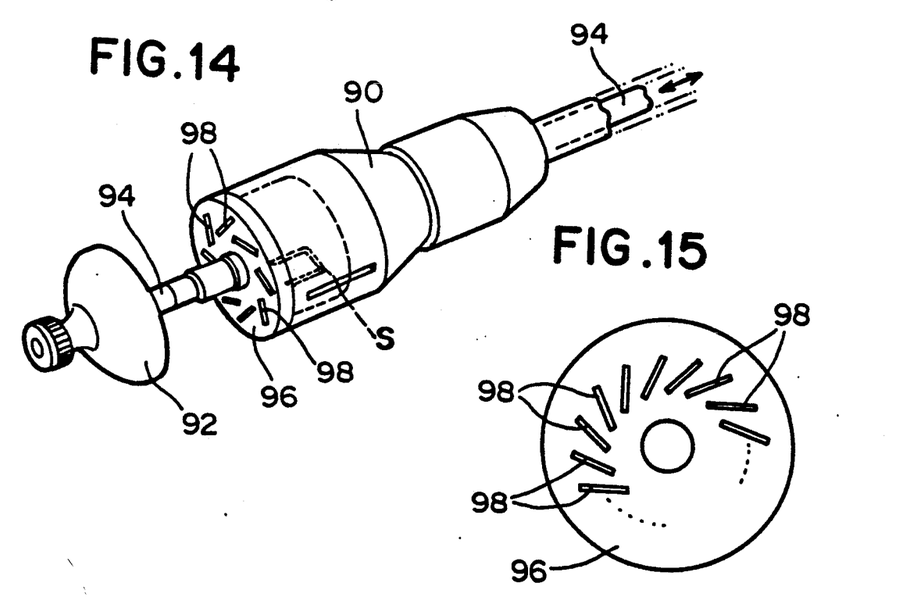
FIG. 14 is a partly perspective view of a further embodiment of this invention.
FIG. 15 is a staple cartridge in FIG. 14.

An embodiment utilizing a cylindrical staple cartridge 96, which is applicable to suturing of tubular tissues, such as an intestine or the like, is illustrated in FIG. 14. The cylindrical cartridge 96 has staple chambers 98 arranged aslant circumferentially and is detachably mounted onto a first jaw 90 as shown in FIG. 15. A second jaw 92 is detachably secured at the leading end of a shaft 94 penetrating the assembled first jaw 90 and cartridge 96, and can open or close relative to the first jaw 90 by operating the shaft 94. Upon putting the tubular tissues to be sutured between the stapler cartridge 96 and second jaw 92, the first and second jaws 90, 92 are forcibly closed by drawing the shaft 94. While closing the first and second jaws, the staples (S) loaded within the staple cartridge 96 are discharged toward the second jaw 92 and thrust into anvil grooves formed in the second jaw 92 to cause the legs of the staples to be inserted through the tissues and bend inwardly. Thus, the tissues are steadily sutured while arresting hemorrhage as desired.

As is clear from the foregoing, the surgical stapler according to the present invention employs the detachable staple cartridge which can readily be fitted into the stapler so that the stapler can be easily and promptly loaded with suturing staples even in the middle of a surgical operation. Therefore, the stapler of this invention insures ease of handling and proves advantageous from the standpoint of safety in a surgical operation. Also, since the staple cartridge is detachable, as touched upon above, the staples contained in the staple cartridge can be visually discerned with ease so as to prevent faulty suturing. Besides, by providing the staple cartridge with magnetic force, the metal staples can be securely retained within the staple cartridge so as to prevent the staples from falling out of the staple cartridge accidentally.

As can be readily appreciated, it is possible to deviate from the above embodiments of the present invention and, as will be readily understood by those skilled in this art, the invention is capable of many modifications and improvements within the scope and spirit thereof. Accordingly, it will be understood that the invention is not to be limited by these specific embodiments, but only by the scope and spirit of the appended claims.

What is claimed is:

1. A surgical stapler, comprising:
   a first jaw having a plurality of staple extruding pieces thereon;
   a second jaw having at least one row of anvil grooves, each said anvil groove comprising at least one arc-shaped bottom surface comprising a single arc having a length substantially equal to the height of the leg portions of a staple, and said anvil grooves of said at least one row being arranged aslant relative to the direction of said at least one row of anvil grooves;

a cartridge holding member mounted between said first and second jaws and having a cartridge hole;

a staple cartridge having at least one row of staple chambers therein into which staples can be inserted, said staple cartridge being detachably fitted into said cartridge hole in said cartridge holding member, said staple chambers being located opposite to said staple extruding pieces and said anvil grooves, and said staple chambers of said at least one row being arranged aslant relative to the direction of said at least one row of staple chambers;

wherein said first jaw, said cartridge holding member and said second jaw are pivotally connected by a first axial pin, a first handle is connected to said first jaw by a second axial pin, and a second handle is connected to said second jaw through a third axial pin;

wherein said first and second handles are pivotally connected by a fourth axial pin so as to open and close said first and second jaws by operating said first and second handles; and wherein each said anvil groove has two said arc-shaped bottom surfaces staggered in position relative to each other in the lengthwise direction.

2. The surgical stapler according to claim 1, wherein said staple cartridge has two rows of said staple chambers.

3. The surgical stapler according to claim 1, wherein said staple cartridge has two rows of said staple chambers, the second said row having said staple chambers arranged in a line in the direction of said second row.

4. The surgical stapler according to claim 1, wherein said two arc-shaped bottom surfaces of each said anvil groove extend in lengthwise directions laterally adjacent to each other.

5. The surgical stapler according to claim 1, wherein said staple cartridge has a magnetic member for attracting staples magnetically.

6. The surgical stapler according to claim 1, wherein said staple cartridge is made of a magnetic material and is magnetized.

7. The surgical stapler according to claim 1, wherein said cartridge holding member has a step portion formed in the lower surface thereof about said cartridge hole, and said stapler cartridge has a flange for engaging said step portion.

8. The surgical stapler of claim 1, wherein two rows of said anvil grooves are provided, both said rows of anvil grooves being arranged aslant, and two rows of said staple chambers are provided, both said rows of staple chambers being arranged aslant.

9. The surgical stapler of claim 8, wherein said rows on said second jaw have a ditch therebetween formed in the surface of said second jaw.

* * * * *